United States Patent [19]
Bolton et al.

[11] Patent Number: 5,527,713
[45] Date of Patent: Jun. 18, 1996

[54] ANTI-CD3 ANTIBODY-AMINODEXTRAN CONJUGATES FOR INDUCTION OF T-CELL ACTIVATION AND PROLIFERATION

[75] Inventors: Wade E. Bolton, Davie; John A. Maples, Miami Shores; Olavi Siiman, Davie; Norma S. Kenyon, Coral Gables; Cynthia G. Healy, Miami, all of Fla.

[73] Assignee: Coulter Corporation, Miami, Fla.

[21] Appl. No.: 504,327

[22] Filed: Jul. 19, 1995

Related U.S. Application Data

[63] Continuation of Ser. No. 75,647, Jun. 11, 1993, abandoned.
[51] Int. Cl.$^6$ .................................................. G01N 33/548
[52] U.S. Cl. ..................... 436/529; 436/528; 436/547; 436/548; 530/388.1; 530/391.1; 530/391.5
[58] Field of Search .................................. 436/528, 529, 436/547, 548; 530/388.1, 391.1, 391.5

[56] References Cited

U.S. PATENT DOCUMENTS 4,925,648  5/1990  Hansen et al. ............................ 424/1.1

FOREIGN PATENT DOCUMENTS 9004633  5/1990  WIPO.

OTHER PUBLICATIONS

Geller, "Role of Cross-Linking in stepwise Activation of T cells", Scand. J. Immunol., 35, 1992, pp. 327–334.

Dixon et al, "Activation of Human T Lymphocytes by Crosslinking of Anti-CD3 Monoclonal Antibodies", Journal of Leukocyte Biology, 46, 1989, pp. 214–220.

M. Brunswick, et al., "Picogram Quantities of Anti-Ig Antibodies Coupled To Dextran Induce B Cell Proliferation," J. Immuno. 140: 3364–3372 (1988).

S. Panzer et al., Scand. J. Immunol. 32: 359–371 (1990), "Purified Human T Cells Stimulated With Cross-Linked Anti-CD3 Monoclonal Antibody OKT3: rIL-1 is a ... ".

Y. Manabe et al., J. Lab. Clin. Med. 104: 445–454 (1984) "Production Of A Monoclonal Antibody-Methotrexate Conjugate Utilizing Dextran T-40 ... ".

L. B. Shih et al., Int. J. Cancer 41: 832–839 (1988), "Site-Specific Linkage Of Methotrexate To (MAb) ... Using An Intermediate Carrier".

D. A. Hafler et al., J. Immunol. 142: 2590–2596 (1989), "Mechanisms Of Immune Memory: T Cell Activation ... ".

J. W. Bulte et al., Mag. Res. in Med. 25: 148–157 (1992), "Specific MR Imaging ... Antibody-Guided Dextran-Magnetite Particles".

A. R. Oseroff et al., Proc. Natl. Acad. Sci. USA 83: 8744–8748 (1986), Antibody-Targeted Photolysis ... Using Antibody-Chlorin Conjugates.

S. C. Meuer et al., J. Exp. Med. 158: 988–993 (1983), Antigen-Like Effects ... On Human T Cell Clones.

A. Altman, et al., Crit. Revs. in Immunol. 10: 347–391 (1990), "T Lymphocyte Activation: A Biological Model Of Signal Transduction".

P. K. A. Mongini J. Immunol. 148: 3892–3901 (1992), "Membrane IgM-Mediated Signaling Of Human B Cells".

H. Maeda, et al., Bioconjugate Chem. 3: 351–362 (1992), "Conjugates Of Anticancer Agents And Polymers: Advantages Of Macromolecular Therapeutics In Vivo".

Primary Examiner—James C. Housel
Assistant Examiner—Christopher L. Chi
Attorney, Agent, or Firm—Michelle A. Kaye

[57] ABSTRACT

The invention describes the use of novel aminodextran compounds containing about 5–20% by weight amine groups to bind a plurality of monoclonal antibodies. The resulting antibody-aminodextran compounds may be used to induce the activation and proliferation of selected mammalian cells. Specific examples are given using an anti-CD3 monoclonal antibody conjugated two aminodextrans containing about 5% and 16%, respectively, by weight amine groups as an agent for inducing the activation and proliferation of T cells.

9 Claims, 4 Drawing Sheets

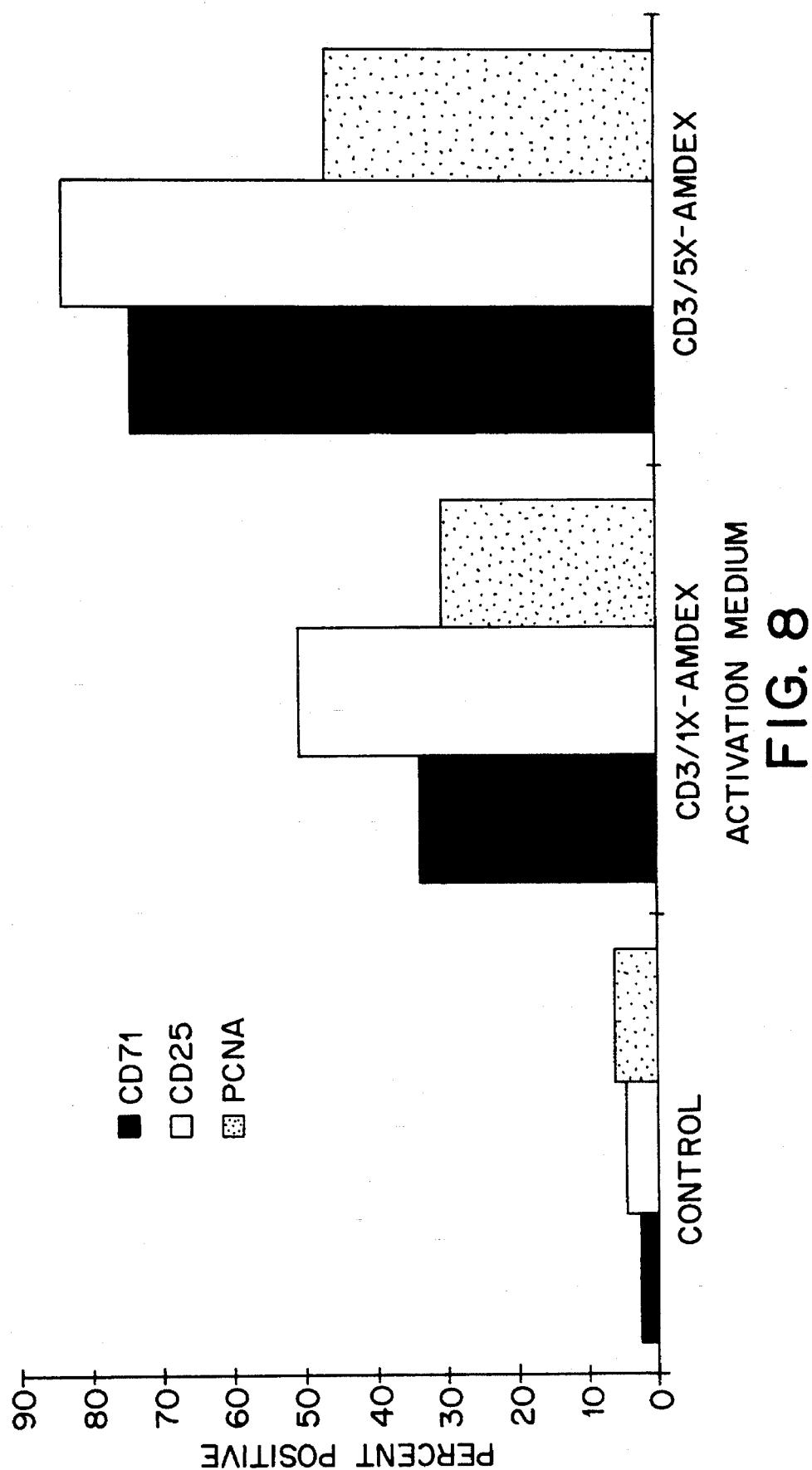

ANTI-CD3 ANTIBODY-AMINODEXTRAN CONJUGATES FOR INDUCTION OF T-CELL ACTIVATION AND PROLIFERATION

This is a continuation of application Ser. No. 08/075,647 filed on Jun. 11, 1993 now abandoned.

RELATED INVENTIONS

This application is related to U.S. Pat. No. 5,248,772 entitled FORMATION OF COLLOIDAL METAL DISPERSIONS USING AMINODEXTRANS AS REDUCTANTS AND PROTECTIVE AGENTS, issued Sep. 28, 1993; and co-pending applications entitled POLYMERIC PARTICLES HAVING A BIODEGRADABLE GELATIN OR AMINODEXTRAN COATING AND PROCESS FOR MAKING SAME, Ser. No. 07/961,157, filed Oct. 15, 1992; and BIODEGRADABLE GELATIN-AMINODEXTRAN PARTICLE COATINGS AND PROCESS FOR MAKING SAME, Ser. No. 07/968,158, filed Oct. 29, 1992, which is a Continuation-In-Part of U.S. Pat. No. 5,169,754, issued Dec. 8, 1992, entitled BIODEGRADABLE PARTICLE COATING HAVING A PROTEIN COVALENTLY IMMOBILIZED BY MEANS OF A CROSSLINKING AGENT AND PROCESS FOR MAKING SAME. This application and the related applications and patent are wholly owned by a single common assignee, Coulter Corporation, Miami, Fla. The teachings of these patents and copending applications are incorporated herein by reference.

FIELD OF THE INVENTION

The present invention relates to the use of novel antibody-aminodextran conjugates for use in inducing the activation and proliferation of leukocytes. In particular, the invention relates to the use of an anti-CD3 monoclonal antibody covalently coupled to an aminodextran. The covalently coupled antibody-aminodextran conjugates have application in the analysis of immune cell functions in patients with various medical conditions, such as AIDS and other immunodeficiencies, infectious diseases, cancers, autoimmunity, and atopic diseases. In addition, the leukocytes from recipients of transplanted cells and/or tissues can be functionally evaluated utilizing this technology.

BACKGROUND OF THE INVENTION

Immunosuppression, whether induced by drugs or disease, can lead to alterations in T cell and/or accessory cell function. For example, it has been demonstrated that AIDS patients manifest defective responses to mitogens, autoantigens, alloantigens, and soluble antigens. This altered immunoreactivity is attributable to defects in both responding (T) and stimulating (monocyte and dendritic) cell populations. Decreased CD4 expression on the monocytes obtained from AIDS patients has been demonstrated, yet no decrease in monocyte count has been observed. Immunosuppressive drugs can also alter antigen presenting cell function. As a result of these observations, it has been determined that a method for specifically stimulating T cells which did not rely on the presence of monocyte or dendritic cells would be desirable.

While there are numerous methods of activating T cells, the optimal method appears to require the multivalent interaction of antibodies, or other receptor binding species such as lectins, with the T cell antigen receptor/CD3 complex [hereafter TCR/CD3] on the surface of T cells. [A. Altman et al., Crit. Revs. in Immunol. 10:347–391 (1990)]. CD3 specific monoclonal antibodies can induce highly purified, resting T cells to proliferate, provided, however, that there is present a mechanism for crosslinking the antibody-bound TCR/CD3 complexes. Numerous authors have shown that the crosslinking requirement can be met by binding the antibody to a substrate, for example, Sepharose® beads [S. Meuer et al., J. Exp. Med. 158:988–999 (1983) and D. A. Hafler et al., J. Immunol. 142:2590–2596 (1989)], polystyrene beads [S. Panzer et al., Scand. J. Immunol. 32:359–371 (1990)], or tissue culture dishes. International Patent Publication WO 90/04633 describes solid-state supported monoclonal antibodies for induction of T cell activation and the growth of T cells. Accessory cells, for example, monocytes, can also fulfill the need for crosslinking by means of Fc receptor mediated binding of the T cell bound anti-CD3 monoclonal antibodies to the monocyte cell surface.

The parameters used to assess cellular activation were reviewed by A. Altman et al., Crit. Revs. in Immunol. 10: 347–391 (1990). Cell activation has been measured by changes in nucleic acid synthesis, protein or glycoprotein synthesis, cellular size and morphology, membrane integrity, expression of cellular constituents, cell function, cell growth, cell differentiation and the release of cellular components. These cellular changes have been detected by numerous different methods, many of which are described in the patents and publications cited herein. Historically, the diagnosis of immune deficient conditions has been done using laboratory tests in which various stimuli are applied to T cells in order to determine if they can be activated in vitro. Deficient T cell reactivity has been tested by stimulation with mitogens, alloantigens and soluble antigens [R. Hong in Manual of Clinical Immunology, 2nd Ed., N. R. Rose and H. Friedman, eds. (American Society for Microbiology 1980), Chapter 111, pages 833–849]. However, these methods are not specific for all T cells. Mitogens activate both T and B cells. Alloantigens activate only those selected T cells which have the appropriate receptor type. The response to soluble antigens, for example, tetanus toxoid, can be effected by a patient's immunization history. The anti-CD3 aminodextran conjugates of the claimed invention specifically activate all CD3 positive cells and thus avoid these problems. The CD3 antigen is found on virtually all mature peripheral T lymphocytes. This antigen is a component of the T cell receptor complex and is non-covalently linked to a polymorphic, clonotypic structure termed Ti. Antibodies to the CD3 surface structure serve as probes for constant regions of the T cell receptor which is exclusively expressed on immunocompetent T lymphocytes. Consequently, quantifying immunocompetent T cells using this antibody is rapid and efficient.

In addition to the forementioned copending applications, particles coated with dextran or dextran derivatives have been described by R. J. Mrsny et al., Eur. J. Cell. Biol. 45:200–208 (1987) (ouabain-aminodextran-gold particles); J. W. M. Bulte et al. Magn. Reson. Med. 25:148–157 (1992) (biotinylated dextran-magnetite particles). The use of antibody-dextran type substances as carriers has been described by U. Manabe et al., J. Lab Clin. Med. 104:445–454 (1984) (antibody-polyaldehyde dextran-methotrexate); A. R. Oseroff et al., Proc. Natl. Acad. Sci. USA 83:8744–8748 (1986) (antibody-aminodextran-chlorin); and S. Rakestraw et al., Proc. Natl. Acad. Sci. USA 87:4217–4221 (1990) (antibody-dextran hydrazide-Sn(IV) chlorin). Other conjugated and crosslinked species have been described by S. S. Wang in "Chemistry of Protein Conjugation and Crosslinking" (CRC Press, Boca Raton, Fla. 1991) and H. Maeda et al., Bioconjugate Chem. 3:351–362 (1992). The standard procedure for the introduction of amine groups into dextran has been to first cleave the sugar rings to form polyaldehyde-dextran. The second step is to react the cleaved rings with a diamine such as ethylenediamine or 1,3-diaminopropane to form a Schiff's base complex. The Schiff's base is then stabilized by reduction with sodium borohydride. The "aminodextran" compounds as described in the above cited art were ill-described, typically lacking either elemental analyses or even average molecular weight determinations. Furthermore, the periodate oxidation method of preparing aminodextrans as described in these publications resulted in a low percentage of amino groups per molecule. The percentage was less than 4–5 percent. Higher degrees of amine substitution were not possible under the usual conditions of the prior art because high diamine concentrations caused extensive aminolysis of the glucosidic linkages between the sugar rings in dextran which resulted in very low molecular weight fragments. As a result, the yields of polymeric aminodextran derivatives were low and decreased drastically as higher and higher degrees of amine substitution were pursued.

An alternative method of producing aminodextrans is by carboxymethylation of sugar residue hydroxyl groups in chloroacetic acid, followed by carbodiimide coupling of a diamine such as ethylenediamine. M. Brunswick et al., J. Immunol 140:3364–3372 (1988) and P. K. A. Mongini et al., J. Immunol. 148:3892–3902 (1992) used this method to produce an aminodextran having about one amine group per sixty-seven glucose residues (1/67). These authors then used the aminodextrans to prepare anti-Ig antibody-aminodextran conjugates for use in inducing B cell activation and proliferation.

The claimed invention teaches the use of anti-CD3 monoclonal antibodies conjugated to aminodextrans as a method of providing for the specific stimulation of T cells. Analysis of T cell function is critical to the diagnosis of immunodeficiency. For example, the CD3-aminodextran conjugates described herein provide a uniquely specific method for activating the T cells used for T cell analysis in AIDS patients. M. Clerci et al., J. Clin. Invest. 84:1892–1899 (1988) found that an in vitro T helper cell ($T_H$) assay "can detect multiple stages of immune dysregulation early in the course of HIV infection". Tetanus toxoid and alloantigens, which have selectivity problems as stated above, were used as stimuli for T cells. S. C. Muluk et al., Transplantation Proceedings 23:1274–1276 (1991) have shown that T cell monitoring can be useful for determining the efficacy of immunosuppressive agents in transplant patients.

The claimed invention teaches the use of aminodextrans, particularly aminodextrans having a high degree or percentage of amine substitution, as a means of crosslinking antibodies and of using the resulting antibody-aminodextran conjugate to induce activation and proliferation of T cells. Aminodextrans have been used in the copending applications cited herein to coat polystyrene microspheres and magnetic and non-magnetic particles such as ferrite and metallic gold particles. The aminodextran coated particles are then used to covalently link various monoclonal antibodies. Both the degree of amine substitution and the degree of polymerization of the dextran can be varied to determine the optimal form of the resulting coated particle to which an antibody can be conjugated. Non-specific interactions between antibody-aminodextran coated particles and cells are minimized by blocking amine groups with excess crosslinking agent which, in turn, is also blocked.

SUMMARY OF THE INVENTION

The invention relates to the use of aminodextrans having 5–20% by weight amine groups as crosslinking agents for monoclonal antibodies to produce antibody-aminodextran conjugates that are useful in the induction and activation of mammalian cells and especially human cells. In particular, the conjugates find utility for inducing the activation and proliferation of human T and B cells. A preferred embodiment of the invention is the preparation and use of anti-CD3 monoclonal antibodies conjugated to aminodextrans to induce T cell activation and proliferation. The invention further describes the use of novel aminodextrans having a high degree of amine substitution (greater than 10%) in the formation of such conjugates and compares the results with conjugates formed using aminodextrans generally known in the art which typically have about 4–5% amine substitution. Comparative results indicate that the use of aminodextrans with high amine content is preferred.

The invention also relates to a method of analyzing mammalian T cells, particularly human cells. A sample containing or thought to contain T cells is reacted with an aminodextran/anti-T-cell monoclonal antibody prepared as described herein. The resulting aminodextran-antibody-cell complex, after any appropriate incubation time, may be analyzed to evaluate T cell functions or changes in T cell function. Tests which may be used in such analysis comprise changes in nucleic acid (DNA or RNA) synthesis, protein or glycoprotein synthesis, cellular size and morphology, membrane integrity, expression of cellular constituents and the release of cellular components into the medium containing the cells undergoing analysis. Typical diseases or disorders which are amenable to this type of analysis are AIDS, other non-AIDS immunodeficiency diseases, infectious diseases, cancer, autoimmunity disorders and atopic disorders. The method also may be used to test T cells from patients who are the recipients of tissue, organ or cell transplants. In those cases involving transplants, prior to the T cell analysis, non-T leukocyte cells and their immature precursors may be stimulated to facilitate additional testing related to conditions arising from the transplant. The non-T cells include B cells, macrophages/monocytes, dendritic cells, neutrophils, eosinophils, basophils, cytotoxic effector cells, hematopoietic stem cells and the immature precursor cells of each of these cells. Methods stimulating such non-T cells and their precursor cells are described in the publications cited in this application.

BRIEF DESCRIPTION OF THE DRAWINGS

FIG. 8 graphically illustrates the effect of selected anti-CD3/Amdex conjugates on the percentage of CD25, CD71, and PCNA positive cells.

DETAILED DESCRIPTION OF THE INVENTION

Figure 1:
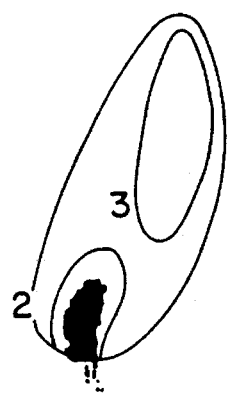
FIG. 1 illustrates the distribution of cells in the forward versus side scatter histogram of a sample containing unactivated, control T cells.
Figure 2:
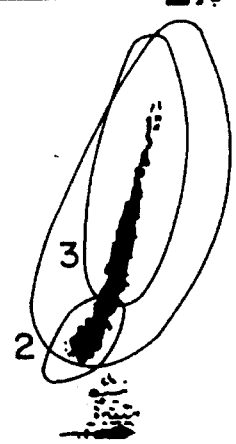
FIG. 2 illustrates the distribution of cells in the forward versus side scatter histogram of a sample containing T cells activated by the use of an anti-CD3/1X-Amdex conjugate.
Figure 3:
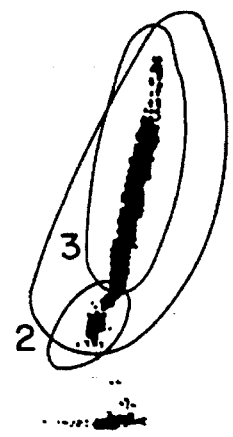
FIG. 3 illustrates the distribution of cells in the forward versus side scatter histogram of a sample containing T cells activated by the use of an anti-CD3/5X-Amdex conjugate.

Crosslinked antibodies show enhanced ability to induce resting T cells in the $G_0/G_1$ phase to progress into the readily observable $S,G_2/M$ phases of the cell cycle, including DNA synthesis. Soluble polymers such as aminodextran, which have been used to coat a variety of colloidal particles, should be suitable crosslinking agents for antibodies used to initiate and sustain T cell proliferation. While aminodextrans have been used in conjugates keyed to the stimulation of B cells, they have not been used with T cells. We describe herein improved methods for preparing aminodextrans, particularly those with greater than 10% amine substitution, and their use in the formation of antibody-aminodextran conjugates which are subsequently used for stimulating the activation and proliferation of mammalian cells and especially for stimulating T cell activation and proliferation. Both the degree of amine substitution and the degree of dextran polymerization can be varied to find the optimal form of the aminodextran to be used as an antibody carrier and crosslinking agent.

The examples provided herein are for illustrating the invention and are not to be construed as limiting the invention. For example, while the examples herein describe the induction of human T cell activation and proliferation, the proper choice of antibodies may extend the utility to other cells, such as a B cell, and other mammalian species, such as a cat, dog or horse.

Two forms of aminodextran were used to form the conjugates described herein. The first, which is described below as 1X-aminodextran (abbreviated 1X-Amdex), has a degree of substitution equal to about 1/32 (two 1,3-diaminopropane groups per sugar residue) and an average molecular weight of about 1,000,000 daltons. The second, described below as 5X-aminodextran (abbreviated 5X-Amdex), has a degree of substitution equal to about 1/7 and an average molecular weight of about 350,000 daltons.

The anti-CD3 monoclonal antibody used herein was obtained from Coulter Corporation, Miami, Fla. and was activated for conjugation to the aminodextran by iminothiolane using standard procedures. The source of the anti-CD3 monoclonal antibody or other T cell activating monoclonal antibodies is not critical to the invention and other sources of such antibody may be used in place of that described herein. The aminodextrans were activated with the heterobifunctional reagent sulfo-SMCC [sulfosuccinimidyl-4-(N-maleimidomethyl) cyclohexane-1-carboxylate] prior to conjugation with the activated antibody. The invention is not limited to the use of iminothiolane and sulfo-SMCC as activating agents. Those skilled in the art will recognize that other reagents, such as those described in U.S. Pat. No. 5,169,754 and the other related applications, may be used in place of the iminothiolane and sulfo-SMCC used herein.

The Methods A–C described herein and in copending application Ser. Nos. 07/968,158 and 07/827,347 may be used to prepare aminodextrans having an amine content in the range of greater-than-zero to about twenty percent. Method C is preferred for preparing aminodextrans having more than 5% amine groups; particularly, for amirouextrans having more than 10% amine groups. The use of the hollow fiber cartridge described herein places a lower molecular weight limit of 5,000 daltons on the aminodextrans prepared using such cartridge. This lower limit may be raised or lowered by changing the choice of cartridge used in the process. The maximum molecular weight of the aminodextran products is limited to that of the starting dextran materials. Aminodextrans prepared by oxidative cleavage methods known in the art have a maximum of 4–5% amine group. The methods described herein allow for the preparation of aminodextrans having 300% to 400% more amine groups than the aminodextrans described in the art.

Antibodies other than the Coulter T3 antibody described herein have also been used according to the invention. These include an anti-CD2 antibody (Coulter T11, IgG1), and an antibody against an 85,000 dalton species expressed on the gamma chain of the T cell receptor (Coulter TiGamma, IgG1) among others. An anti-CD3 monoclonal antibody such as T3 is preferred.

When the invention is used in conjunction with methods of stimulating non-T cells and their precursor cells the methods used are those found in the technical literature and known to those skilled in the art. For example, if one wishes to analyze and/or evaluate B cells as well as T cells, one may use anti-IgD and anti-IgM monoclonal antibodies as described by M. Brunswick et al. in J. Immunology 140: 3364–3372 (1988). In such a case, the dextran or Ficoll used by Brunswick et al. may be replaced by the aminodextrans disclosed herein. If one wished to stimulate and activate macrophages, one may use a poly(styrene-comaleic n-butyl ester)-conjugated neocarzinostatin as taught by H. Maeda et al. in Bioconjugate Chemistry 3: 351–362 (1992).

I. Preparation of Aminodextrans.

Method A. Small scale preparation of aminodextran.

Aminodextran was prepared by partial cleavage and oxidation of the glucopyranose rings in dextran to give aldehyde functional groups, coupling of the aldehyde groups with 1,3- diaminopropane to form Schiff base linkages and reduction of the Schiff's base linkages to form stable carbon-nitrogen bonds. In a typical procedure, 20 g of dextran were dissolved in 150 ml of 50 mM potassium acetate buffer, pH 6.5. A solution of 2.14 g of sodium periodate in 25 ml of distilled water was added dropwise to the dextran over about 10 minutes using vigorous magnetic mixing. The resulting solution was stirred at room temperature, 15°–27° C., for about 1.5 hours and then dialyzed against distilled water. 20 ml of 1,3-diaminopropane were mixed with 20 ml of distilled water, cooled in an ice bath, vigorously stirred and pH adjusted from about 11.5 to about 8.7 over about 15 minutes by the addition of glacial acetic acid. Typically, 15–20 ml of glacial acetic acid were used. The dialyzed dextran solution was added dropwise over about 15–20 minutes to the chilled diamine solution. After the addition was completed, the resulting solution was stirred at room temperature for about 2.25 hours. A reducing solution of 0.8 g sodium borohydride in 10 ml of 0.1 mM sodium hydroxide was added to the dextran reaction mixture at room temperature over about 15 minutes. The reaction mixture was stirred during the borohydride addition to expel most of the effervescence. The crude aminodextran solution was exhaustively dialyzed against distilled water until the conductivity of the effluent was 3–4 μmho/cm. The dialyzed solution was then filtered through a 0.2 μm filter and freeze-dried over 24 hours in a model TDS-00030-A, Dura-Dry® microprocessor controlled freeze-dryer (FTS Systems, Inc.) to produce 4.25 g of flaky, pale yellow crystals in 21% yield.

Method B. Large scale preparation of aminodextran.

The procedure of Method A was modified for the large scale preparation of aminodextran and for increasing the number of amine groups introduced into dextran. Hollow fiber membrane filtration replaces dialysis and a smaller diamine-periodate molar ratio was used to avoid further cleavage of the sugar polymer into lower molecular weight fragments. These changes also serve to shorten the contact time between excess diamine and substituted dextran during the removal of excess low molecular weight reagents. Without these changes, the aminolysis of the glucosidic linkages in high molecular weight dextran (e.g. dextran T-2M) was very extensive and drastically reduced the yield of aminodextran above a cut-off molecular weight of 5,000 daltons. A hollow fiber cartridge (polysulfone, 3 ft² membrane surface area, 1 mm diameter fibers and 5,000 MW cut-off model UFP-5-E-6, A/G Technology Corp.) was mounted vertically with an input power pump (two pump heads, maximum flow rate of about 4.56 liters/minute with No. 18 Norprene® food grade tubing) delivering 15–20 psi which corresponds to 5–10 psi in the retentate line. The filtrate was collected at 50–100 ml/min. Washing was done using 20–30 liters of distilled water over about 6–8 hours. The specific conductance was reduced to about 3–4 $\mu$mho-cm$^{-1}$ and the pH was 6.0–6.5. The feed volume was maintained at 2 liters during desalting and then concentrated to 800 ml in the first washing of oxidized dextran and to 400 ml in the second washing of The feed volume was maintained at 2 liters during desalting In a standard scaled-up preparation, 80 g of dextran were transferred to 1 quart [liter] glass blender bowl containing 600 ml distilled water. The solid was blended for about 2–5 minutes at medium speed to dissolve all the dextran. 8.56 g of sodium periodate were dissolved in 100 ml of distilled water and the resulting solution was added dropwise to the dextran solution over about 10 minutes using vigorous magnetic stirring. After the addition was completed, the resulting mixture was stirred at room temperature for an additional 3 hours. The resulting viscous reaction mixture was then diluted to 2 liters with distilled water and desalted using a hollow fiber cartridge. The initial specific conductance was 1.5 mmho-cm$^{-1}$ or higher and the initial pH was 4.0. About 18–22 liters of distilled water were used to obtain a solution having a final pH of 6.0–6.5. The final volume of washed, oxidized dextran solution was 800 ml.

To the washed, oxidized dextran solution, 80 ml of colorless, liquid 1,3-diaminopropane were slowly added over about 10 minutes at room temperature. The resulting mixture was then stirred at room temperature for an additional 3 hours. After the stirring was finished, 3.2 g of sodium borohydride dissolved in 40 ml of 1 mM aqueous sodium hydroxide were added to the room temperature aminodextran reaction mixture over about 5 minutes with magnetic stirring. After the completion of the sodium borohydride addition, the resulting mixture was stirred for an additional 1 hour and then desalted using a hollow fiber cartridge. The initial specific conductance was 5.0 mmho-cm$^{-1}$ or higher and the initial pH was about 12.0. About 20–25 liters of distilled water were needed to reduce the specific conductance to about 3–4 $\mu$mho-cm$^{-1}$ and the pH to 6.0–6.5. The final volume of aminodextran solution was 400 ml. This solution was passed through a 0.2 $\mu$m sterile cellulose acetate filter unit and then freeze-dried over 48 hours to obtain 48 grams of flaky, pale yellow crystals, a 52% yield.

Elemental analyses (C,H,N) were obtained for two samples of aminodextran prepared from dextran T-2M by the methods described above. The analyses are:

Sample 1. 20 g dextran scale, Method A (desalting by dialysis). Obsd.: C, 43.04; H, 6.60; N, 1.09; O (by difference), 49.27. Calculated for $C_{46}H_{79}NO_{37} \cdot 3H_2O$: C, 42.76; H, 6.63; N, 1.08; O, 49.53.

Sample 2. 80 g dextran scale, Method B (desalting by membrane filtration). Obsd.: C, 42.53: H, 6.52N, 1.01; O (by difference), 49.94 Calculated for $C_{49}H_{84}NO_{40} \cdot 3H_2O$: C, 42.61; H, 6.57; N, 1.01; O, 49.81

The analyses for aminodextran in the two preparations were very similar, thus indicating that the same product was obtained whether desalting was done by dialysis or by membrane filtration and whether acetate buffer was used or not used. The yield of aminodextran, however, was raised by 31% in Method B over that in Method A. The empirical formula obtained for Sample 1, $C_{46}H_{84}NO_{40}$, is very similar to the formula $C_{46}H_{79}NO_{37} \cdot 3H_2O$ based on 29 units of glucose ($C_6H_{10}O_5$), 1 unit of fully diamine-substituted sugar ring ($C_{12}H_{28}N_4O_3$ two mol diamine per mol sugar unit,) and twelve units of water. Therefore, the degree of diamine substitution of sugar residues in dextran was 1/30 in Sample 1 in contrast to a theoretical value of 1/12 based on 100% periodate cleavage and diamine substitution according to the balanced oxidation-reduction equation. The empirical formula obtained for Sample 2, $C_{49}H_{90}NO_{43}$, is very similar to the formula $C_{49}H_{84}NO_{40} \cdot 3H_2O$ based on 31 units of glucose, 1 unit of fully diamine substituted sugar ring and twelve units of water. The degree of substitution in dextran by diamine was 1/32 for Sample 2.

Similar results were obtained using aminodextrans having average molecular weights of 10,000, 40,000 and 2,000,000 daltons (T-10, T-40 and T-2M) with 1X (1X=3.3% substitution of sugar residues), 2X (6.6%) 3X (9.9%) and 5X (16.5%) molar amounts of amino groups. All the aminodextrans were initially prepared according to methods A and B using 2 and 3 times the amount of sodium periodate used in the 1X oxidation of dextran. The amount of 1,3-diaminopropane used for Schiff base formation was kept constant.

Modifications have been made to the Methods A and B of preparing aminodextrans which were originally disclosed in Ser. No. 07/827,347. These modifications, disclosed in Ser. No. 07/968,158, involve the oxidation and cleavage of the dextran glucose rings with periodate anion, diamine addition and sodium borohydride reduction of the Schiff's base. The modifications have resulted in increased yield of the aminodextrans, particularly the 5X-aminodextran which was produced in less than 5% yield by the old procedures. Generally, the first modification was to use only a ten percent (10%) excess of diamine over the stoichiometric 2:1 diamine:periodate molar ratio previously disclosed. Second, the diamine addition reaction was conducted at a temperature in the range of about 5°–10° C. Third, the diamine addition reaction was spectroscopically monitored in the near ultraviolet (UV) region for Schiff base formation. Schiff's base formation was deemed completed when successive spectral analyses indicated a plateau was reached. The reaction was then quenched by sodium borohydride addition which reduces the Schiff's base linkages to carbon-nitrogen single bonds and reduces any unreacted aldehyde groups to alcohol groups. These modifications reduced aminolysis of the polymeric sugar groups into lower weight fragments and thus gave higher yield of product after purification and concentration by hollow fiber membrane filtration. The hollow fiber filtration was done using polysulfone cartridge of 3 ft.² membrane surface area, 1 mm diameter fibers having a 5,000 molecular weight cut off. The cartridge was mounted vertically in an input power pump having two pump heads delivering 15–20 psi with a maximum flow rate of 4.56 liter/minute when using No. 18 Norprene® food grade tubing. With this configuration, the pressure in the retenate line was about 5–10 psi. The filtrate was collected at 50–100 ml/min. Washing was done using 20–30 liters of distilled water over about 6–8 hours. The following method for preparing 5X-aminodextran is given to illustrate the modified procedure which is applicable to the preparation of all aminodextrans.

Method C. Preparation of 5X-Aminodextran.

T-2M dextran (50g, 0.308 mol, obtained from Sigma, St. Louis, Mo., or Pharmacia, Piscatawny, N.J.) was added to a 1-quart or 1-liter glass blender bowl containing 300 ml of distilled water. The mixture was blended at maximum speed until all the dextran dissolved, typically about 3–5 minutes. A solution of 26.75 g (0.125 mol) of $NaIO_4$ in 300 ml distilled water was added to the dextran solution over about a 10 minute period using vigorous magnetic stirring. After the periodate addition was completed, the reaction mixture was stirred at room temperature for about an additional three hours. After the three hours, the 600 ml reaction volume had an initial specific conductivity of 9.7 mmho-$cm^{-1}$ and an initial pH of 2.5. The reaction mixture was diluted to two liters with distilled water and desalted using the hollow fiber cartridge. Washing was done using 15–18 liter of distilled water to obtain 600 ml of washed, oxidized dextran solution having a specific conductance of 10 μmho-$cm^{-1}$ and pH of 6.7.

The solution of oxidized dextran was cooled to about 8° C. using an ice bath and 23.2 ml (0.275 mol) of 1,3-diaminopropane was added over about 10 minutes to the oxidized dextran solution. The resulting reaction mixture was stirred and maintained at the ice bath temperature. The formation of the yellow Schiff's base was monitored ever 10–15 minutes by measuring the 335 nm near-UV absorbance of an extracted sample. In a typical experiment, the measurements at 335 nm using a 1 mm path length cell were:

TABLE 1

| minutes | absorbance values |
|---|---|
| 0 | 0.100 |
| 5 | 2.063 |
| 15 | 2.975 |
| 30 | 3.692 |
| 45 | 3.901 |
| 60 | 4.103 |
| 75 | 3.784 |

After the absorbance had reached a plateau, 19.3 g (0.500 mol) of sodium borohydride in 19.3 ml of 1 mM aqueous potassium hydroxide were added to the reaction mixture over about 10 minutes at ambient room temperature using magnetic stirring. After the sodium borohydride addition was completed, the reaction mixture was stirred at ambient room temperature for about an additional two hours. After the stirring was completed, spectroscopic measurement at 335 nm using a 1 cm path length cell gave an absorbance value of 0.067 units which indicates that the Schiff's base compound had essentially disappeared. The reaction mixture, about 1000 ml volume, was then desalted using the hollow fiber cartridge. The initial specific conductance was 43 mmho-$cm^{-1}$ and the initial pH was 11.0. About 18–20 liters of distilled water were used as wash liquid to produce about 300 ml of 5X-aminodextran solution having a specific conductance of about 4–6 μmho-$cm^{-1}$ and a pH of 6.5–7.0. The 5X-aminodextran solution was filtered through a 0.2 μm cellulose nitrate filter and freeze-dried over 48 hours in a model TDS-00030-A, Dura-Dry® microprocessor-controlled freeze-dryer (FTS Systems, Inc.) to produce 24 g (48% yield) of flaky, pale yellow crystals. Elemental analysis: C=45.83%, H=7.00%, N=4.49%, O (by difference)= 42.68%. Calculated analysis for $C_{12}H_{22}O_{8.25}N$: C=46.15%, H=7.10%, N=4.48%, O=42.26%.

The empirical formula based on actual analysis is $C_{12}H_{22}O_{8.3}N$, which is very similar to the formula $C_{12}H_{22}O_{8.25}N$ based on 6 units of glucose per one unit of fully diamine-substituted sugar ring ($C_{12}H_{28}N_4O_3$). Therefore, the degree of diamine substitution in dextran was 1/7 in contrast to a theoretical value of 1/2.5 based on 100% periodate cleavage and diamine substitution.

Repeat experiments using an initial charge of 100 g and 300 g dextran produced a 5X-Amdex product having a similar degree of substitution. The preparation of 1X-Amdex was also scaled up to the 100 g and 300 g levels using Method C. At the 300 g scale the hollow fiber cartridge was changed to a polysulfone membrane of 8.5 ft.$^3$ surface area, 1 mm diameter fibers having a 5,000 nominal molecular weight cut-off (model UFP-5-E-35, A/G Technology Corp.). The cartridge was used for ultrafiltration of both the oxidized dextran and the final aminodextran product to remove salts and low molecular weight reagents or by-products. At the 300 g scale, the yields of the 5X-Amdex and 1X-Amdex products were 135 g (45%) and 162.1 g (57%), respectively. The elemental analysis of the products were: 1X-Amdex, 300 g dextran scale. Obsd.: C, 43.58; H, 6.50; N, 0.82; O (by difference), 49.10 Calculated for $C_{62}H_{105}NO_{50}\cdot2H_2O$: C, 43.79; H, 6.46; N, 0.82; O, 48.92 5X-Amdex, 300 g dextran scale. Obsd.: C, 45.67; H, 6.90; N, 4.04 O (by difference), 43.39 Calculated for $C_{13}H_{24}O_9N$: C, 46.15; H, 7.15; N, 4.14; O, 42.56 The empirical formula obtained for 5X-Amdex, $C_{19}H_{24}NO_9$, is very similar to the formula $C_{13.2}H_{24}NO_{9.5}$ based on 68 units of glucose and one unit of fully diamine-substituted sugar ring. The degree of substitution of sugar residues in dextran was, therefore, about 1/8. The empirical formula $C_{62}H_{110}NO_{52}$ obtained for the 1X-Amdex is similar to the formula $C_{62}H_{105}NO_{50}\cdot2H_2O$ based on 39.3 units of glucose, one unit of fully diamine-substituted sugar ring and two units of water. The degree of substitution of sugar residues in the dextran was, therefore, about 1/40.

II. Preparation of Anti-CD3 Antibody-Aminodextran Conjugate

1. Activation of aminodextran with sulfo-SMCC.

25 mg of 1X-Amdex and 5X-Amdex were dissolved in 6.667 ml portions of 1X PBS in separate, sealable 15 ml tubes to give solutions having a concentration of 3.75 mg/ml. 1X PBS is made by dilution of a 20X PBS solution comprising 53.89 g $K_2HPO_4$, 12.8 g $KH_2PO_4$ and 340 g NaCl in 2 L distilled water as described in copending application Ser. No. 07/961,057. The 1X-Amdex was activated by the addition of 13.5 μL of 10 mg/ml sulfo-SMCC solution per milliliter 1X-Amdex solution (a total of 0.090 ml sulfo-SMCC solution). The 5X-Amdex was activated using five times the amount of sulfo-SMCC solution (0.450 ml). The sulfo-SMCC was pipetted into the respective tubes, vortexed to mix well and then roller mixed for about two hours. After the mixing was completed, each reaction mixture was chromatographed on a separate 100 ml G-50 Sephadex® column (2.5 cm×20 cm) equilibrated with 1X PBS. The samples were eluted using 1X PBS and collected in about 4 ml fractions. Fractions of the first band absorbing at 280 nm contain the high molecular weight activated aminodextran as was verified by Tyndall scatter with a focused light beam. These fractions were pooled to give about 10–11 ml total sulfo-SMCC activated aminodextran in each case. A second, larger band eluted from the column gave no Tyndall scatter. This second band was determined to contain excess low molecular weight sulfo-SMCC reagent.

2. Activation of Antibody.

T3 monoclonal antibody (an anti-CD3 antibody sold by Coulter Corporation) was activated by the addition of 1.423 ml of T3 concentrate (35.14 mg/ml) to a solution comprising 0.323 ml of 2 mg/ml iminothiolane in 1X PBS and 1.587 ml 1X PBS. The resulting solution which had an antibody concentration of 15 mg/ml and an iminothiolane molar concentration fifteen-fold larger was mixed at ambient temperature for about one hour. The entire reaction mixture was then applied to a 100 ml G-50 Sephadex® column equilibrated with 1X PBS and the sample was eluted using 1X PBS. First band peak fractions of about 5 ml volume were combined to give about 10.2 ml of 4.887 mg/ml antibody solution which contains a total of 49.847 mg iminothiolane-derivatized T3 antibody (abbreviated as IT-T3).

3. Conjugation of sulfo-SMCC-aminodextran and iminothiolane-T3 antibody.

5 ml of 4.887 mg/ml IT-T3 solution (about 24.435 ml antibody) were mixed with 10.4 ml of sulfo-SMCC-1X-Amdex (about 25 mg 1X-Amdex) solution for about two hours. In a like manner, 5 ml of 4.887 mg/ml IT-T3 solution were mixed with 11.2 ml of sulfo-SMCC-5X-Amdex (about 25 mg 5X-Amdex) solution. After the mixing was ended, the total volume of each mixture was determined and 0.120 times this volume of 5 mg/ml L-cysteine in 1X PBS was added to each conjugation mixture. The L-cysteine containing mixtures were then mixed for an additional 15 minutes to effect blocking of any unreacted sulfo-SMCC moieties. Lastly, 20 mg/ml iodoacetamide in 1X PBS solution in the amount of 0.120 times the total mixture volume and 1M borate buffer solution, pH 9.8, in the amount of 0.020 times the total mixture volume were added to each mixture. The resulting mixtures were mixed for about 30 minutes to block any unreacted sulfhydryl groups.

4. Purification of anti-CD3-aminodextran conjugates.

The total volume of each conjugation mixture was reduced to about 7.5 ml by centrifuging Amicon Centripep-30 tubes containing the samples for about 20 minutes at about 2500 rpm using a refrigerated Beckman J-6B centrifuge. After centrifuging, the reduced volume mixtures were placed on a Bio-Gel® A-5m agarose column (2.5 cm×48 cm) equilibrated with 1X PBS and chromatographed using 1X PBS as eluent. Eluent fractions of about 4 ml volume were collected using a Pharmacia LKB Frac-100 collector operating in the drop collection mode. The fractions were monitored using a LKB 2138 Uvicord S monitor operating at 280 nm. The first broad band eluted from the column contained the T3 antibody-aminodextran conjugate. A well-separated weaker band of less than half the intensity of the first band was attributed to excess IT-T3 since it showed no Tyndall effect and it had the same retention time on the column as the γ-globulin (Bio-Rad®) standard for gel filtration columns. A strong, well separated third band was assigned to low molecular weight excess blocking reagents. Comparing conjugates made with 1X-Amdex and 5X-Amdex, the T3 antibody-5X-Amdex conjugate had a narrower first band which showed a longer retention time and a very weak second band.

The fractions collected for each conjugate were analyzed at 280 nm using a 1 cm path length cell. Those fractions with an absorbance greater than 0.160 were pooled. The yields were 55 ml of T3-1X-Amdex conjugate having a T3 antibody concentration of 0.301 mg/ml and 54 ml of T3-5X-Amdex conjugate having a T3 antibody concentration 0.317 mg/ml. The results indicate that 66% and 68%, respectively, of the starting antibody was incorporated into the conjugate products. ELISA solid phase assays for T3 in the conjugates gave a T3 antibody concentration of 0.045 mg/ml in T3-1X-Amdex and 0.112 mg/ml in T3-5X-Amdex. The lower ELISA T3 values relative to the $A_{280}$ values might indicate that either that there is some blocking of active T3 antibody sites by conjugation to aminodextran or that there is some interference with the $A_{280}$ reading by an extra absorbance contribution arising from the sulfo-SMCC reagent.

The T3-1X-Amdex and T3-5X-Amdex conjugates were also analyzed by light scatter measurements (90°) using photon correlation spectroscopy. The samples were analyzed using a Coulter® N4MD sub-micron particle analyzer operating in the molecular weight and size distribution processor (SDP) weight analysis modes. Samples of dextran T-2M, 1X-Amdex and 5X-Amdex at a concentration of 10 mg/ml were analyzed. The average molecular weights were $3.1×10^6$ daltons (92%, dextran T-2M), $1.0×10^6$ daltons (100% 1X-Amdex) and $3.5×10^5$ daltons (100% 5X-Amdex). The T3 antibody-aminodextrans prepared above were concentrated to 10 ml total volume before light scatter measurements were made. The average molecular weights were $3.6×10^6$ daltons for T3-1X-Amdex and $1.4×10^6$ for T3-5X-Amdex. Using these results, the T3 antibody:1X-Amdex molar ratio was estimated as $(3,600,000-1,000,000)÷160,000=16:1$ and the T3 antibody:5X-Amdex molar ratio was estimated as $(1,400,000-350,000)÷160,000=6.6:1$.

5. Saturation T3 Antibody Conjugation to Aminodextrans.

The chromatograms of the initial preparation of T3-1X-Amdex and T3-5X-Amdex conjugates showed little, if any, excess T3 antibody when conjugations were done using about 1:1 antibody:aminodextran weight ratios. Consequently, additional experiments were performed using 3:1 T3 antibody: aminodextran weight ratios and the same amount of each aminodextran. The activation, conjugation, blocking and chromatography procedures were the same as those described above. However, during chromatography, a narrow, intense band assigned to excess free IT-T3 trailed the broader T3 antibody-aminodextran band in each case. The IT-T3 band was sufficiently close to the T3-aminodextran bands so that only about half of the first band could be separated in each case. The T3-1X-Amdex preparation thus yielded 75 ml of 0.576 mg/ml T3 in the T3-1X-Amdex solution and 40 ml of 0.466 mg/ml T3 in the T3-5X-Amdex solution. ELISA solid phase assays gave 0.392 and 0.301 mg/ml T3 antibody, respectively. Light scatter results indicate average molecular weights of $6.9×10^6$ daltons and $3.6×10^6$ daltons, respectively. The T3 antibody:aminodextran molar ratio in the conjugates were estimated as $(6,900,000-1,000,000)÷160,000=37:1$ for T3-1X-Amdex and $(3,600,000-350,000)÷160,000=20:1$ for T3-5X-Amdex.

III. Activation of Peripheral Blood T cells With Anti-CD3-Aminodextran Conjugates.

A. Isolation of Peripheral Blood Mononuclear Cells (PBMC).

The procedure used herein was performed at room temperature. Normal whole blood was collected into tubes containing EDTA (ethylenediaminetetraacetic acid). The tubes were centrifuged at 500 g for 10 minutes. Using sterile techniques, the buffy coat was collected, diluted 1:2 (cell:solvent) with 1X PBS and layered over Ficoll-Hypaque®. The resulting sample was then centrifuged at 400 g for 30 minutes, the PBMC interface was collected and diluted with 1X PBS. The diluted sample was centrifuged at 300 g for 10 minutes and then washed twice with 1X PBS by resuspending the pellet, diluting with 1X PBS and centrifuging at 300 g for 10 minutes. After a final resuspension in 1X PBS, the cells were counted and cell viability was ascertained. The cells were divided into two parts, centrifuged as above and resuspended in the appropriate media for the following steps.

B. Culture and Activation of T Cells with Anti-CD3-Aminodextran.

Non-activated cells for use as the control were cultured in Nutricyte® medium containing 10% (v/v) CPSR-2 serum replacement (obtained from Sigma Chemical). The initial cell concentration was $2.5 \times 10^6$ cells/ml. Cultures destined for T cell activation were established in the same medium supplemented with 2–4 ng/ml phorbol 12-myristate 13-acetate (PMA) and 0.125–0.5 µg/ml of anti-CD3-aminodextran. Activated cultures were established using both T3-1X-Amdex and T3-5X-Amdex. The cell suspensions were incubated in T-150 flasks at 37° C., 5% $CO_2$ for 72 hours.

C. Harvesting of Control and Activated Cells.

The control cells and the T3-1X-Amdex and T3-5X-Amdex activated cells were harvested by scraping the bottom of the tissue culture flasks with a disposable scraper, collecting the cells with a pipette and placing them in a centrifuge tube. The cells were counted, centrifuged at 300 g for 10 minutes and washed twice with 1X PBS as has been described.

D. Immunofluorescent Staining and Flow Cytometric Analyses of T Cell Activation.

The degree of T cell activation was determined by immunofluorescent staining of the cells, followed by flow cytometric analysis of the stained cells for the expression of both activation-associated antigens (CD71, transferrin receptor and CD25, IL2 receptor) and proliferation-associated events (DNA and proliferating cell nuclear antigen, PCNA). Aliquots containing $1 \times 10^6$ cells of each culture were placed in six labelled sample tubes (3 sets of six tubes). One tube in each culture set was stained with the following reagents which are sold by Coulter Corporation.

Tube 1: IgG2a-FITC isotype control

Tube 2: IL-2R1-FITC (IgG2a, CD25)

Tube 3: IgM-FITC isotype control

Tube 4: T9-FITC (IgM, CD71)

Tube 5: IgG1, isotype control and propidium iodide (to label DNA)

Tube 6: PCNA (IgG1) and propidium iodide.

For each set of cells (control, T3-1X-Amdex activated and T3-5X-Amdex activated), tubes 1–4 were processed for cell surface staining by incubating the cells with the appropriate FITC conjugated monoclonal antibody for 15 minutes at room temperature. The incubated cells were then diluted with 1X PBS, centrifuged at 300 g for 10 minutes, washed with 1X PBS by suspension and centrifugation and finally resuspended in 1 ml of 1X PBS.

The cells in tubes 5 and 6 were processed for the staining of intracellular antigens by suspending the control cell or activated cell pellets in 1 ml of a solution containing 20 µg/ml lysophosphatidyl choline in 1% paraformaldehyde and incubating the resulting suspensions for 2 minutes at room temperature. After incubation, the cells were resuspended in 1 ml of about −10° C. absolute methanol, incubated on ice for about 10 minutes and centrifuged. The resulting pellet was then incubated in 1 ml of 0.1% NP-40 (available from Sigma Chemical) for about 5 minutes at about 0° C., centrifuged and then incubated again for about 15 minutes at room temperature with IgG1, (tube 5) or PCNA (tube 6) monoclonal antibody. The cells were washed in 1X PBS and incubated for an additional 15 minutes at room temperature with goat anti-mouse immunoglobulin conjugated to FITC. After washing in 1X PBS, 1 ml of propidium iodide was added to each tube.

Samples were analyzed on an EPICS® Profile I flow cytometer equipped with a 488 nm $Ar^+$ ion laser line and a power pack upgrade. Light scattering and fluorescent signals were collected. FL1 represents the FITC fluorescent emission and FL3 represents the fluorescent emission due to propidium iodide. Forward light scatter (FS) was representative of cell size and 90° light scatter (LSS=log side scatter) gives an indication of cell complexity or granularity. For single parameter analysis (CD25 and CD71), a linear cursor was placed on the isotype control histogram such that 2% of the cells were included in the cursor and the majority of cells were excluded (negative control). As a result, CD25 and CD71 positive cells were defined as those cells which emit sufficient fluorescent light to fall within the area defined by the cursor. In the dual parameter analysis for PCNA and DNA, a rectangular analysis region was drawn on the isotype control histogram such that 2% of the cells were included within the rectangle and the majority of cells were excluded (negative control). PCNA positive cells were, therefore, defined as those cells which emitted sufficient fluorescent light to fall within the defined region. As the amount of DNA increases, the amount of propidium iodide taken up by a cell also increases. The percentage of cells in the $G_0/G_1$, S, and $G_2/M$ phases of the cell cycle were determined using the Multicycle® DNA analysis program.

Figure 5:
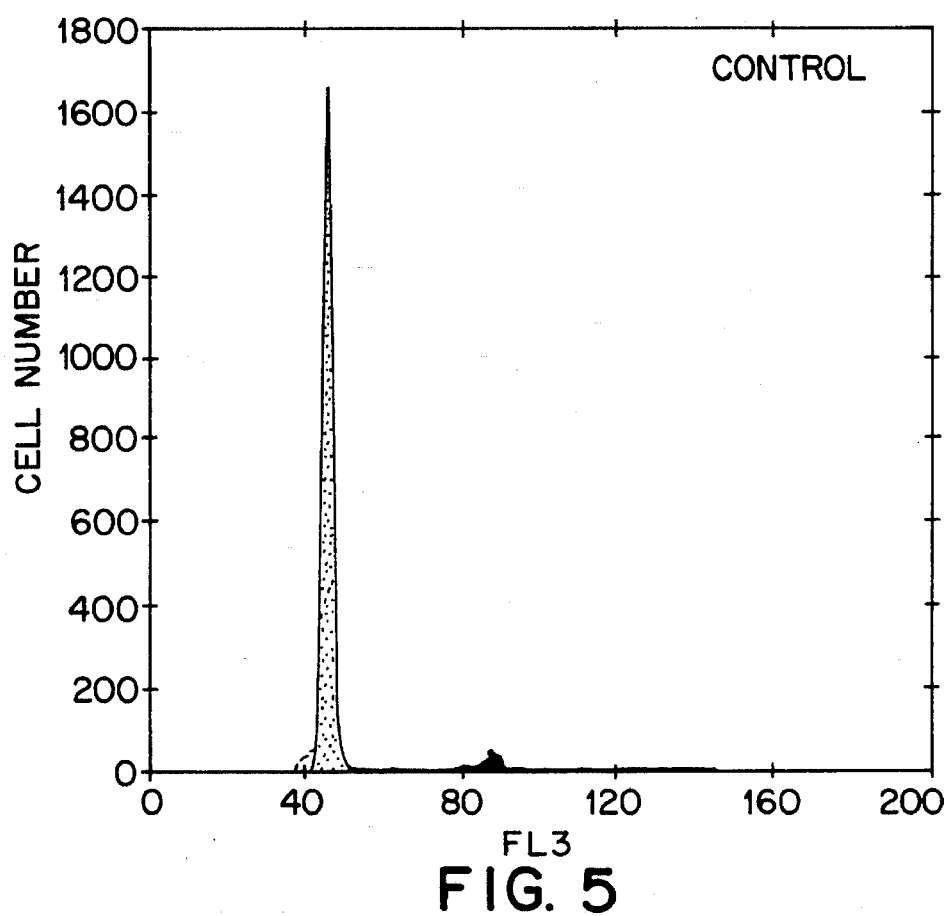
FIG. 5 illustrates the DNA content of control cultured T cells which were not stimulated with anti-CD3/Amdex conjugates.
Figure 6:
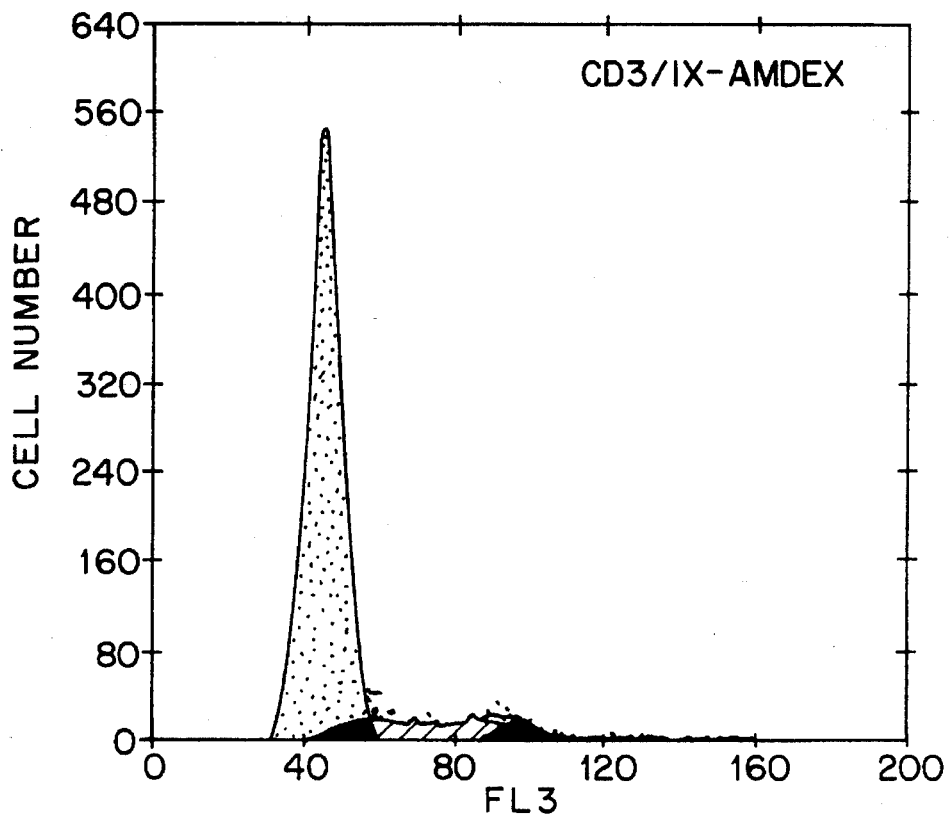
FIG. 6 illustrates the DNA content of T cells activated with anti-CD3/1X-Amdex conjugates.
Figure 7:
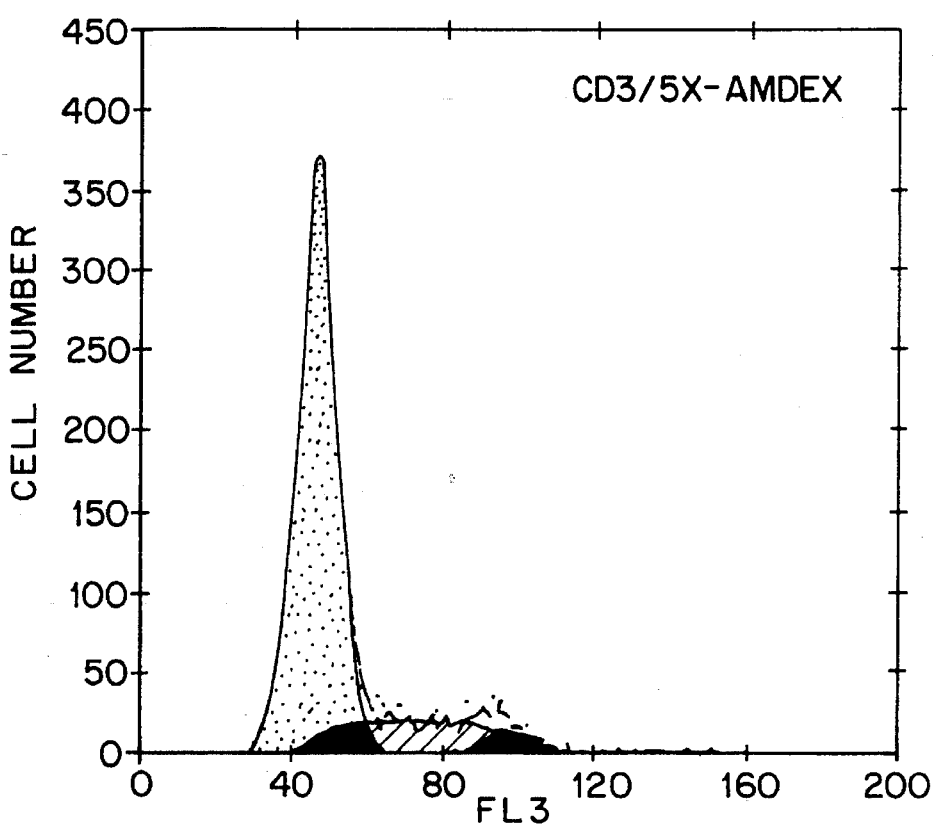
FIG. 7 illustrates the DNA content of T cells activated with anti-CD3/5X-Amdex conjugates.

The analytical results indicate that stimulation with T3-5X-Amdex (saturated) conjugate results in optimal T cell activation as determined by blast cell formation, expression of cell surface activation markers (CD25 and CD71), DNA synthesis and the expression of proliferation-associated antigen (PCNA). As can be determined by a review of FIGS. 1–4, and Table 2, the percentage of activated blast cells, as determined by increased forward and 90° light scatter, was maximal after stimulation with the 5X-Amdex conjugate. The results of Multicycle® analysis of the DNA data also revealed that stimulation with the T3-5X-Amdex conjugate resulted in the greatest percentage of cycling cells (FIGS. 5–7 and Table 2). Similarly, the percentage of CD25, CD71 and PCNA positive cells was optimal after activation with T3-5X-Amdex us shown in FIG. 8 and Table 2.

Anti-CD3 induced activation and proliferation of T cells requires crosslinking of CD3 molecules on the T cell surface. This requirement can be met via Fc mediated binding of anti-CD3 on the monocyte cell surface. The data shown in Table 2 and FIGS. 1–8 was obtained from monocyte containing cultures. T cells were purified and cultured with T3 monoclonal antibody alone or with the T3 antibody conjugated to 5X aminodextran in order to verify that the enhanced T cell activation and proliferation observed was due to the use of the 5X-Amdex conjugate. Peripheral blood mononuclear cells (PBMC) were obtained via density gradient centrifugation over Ficoll-Hypaque® and the majority of monocytes were removed via adherence to plastic over a period of 90 minutes. B cells and residual monocytes were depleted with B4 and Mo2 conjugated magnetic beads, and the essentially pure T cells (>95% as determined by immunofluorescence analysis) were cultured as previously described. The results, given in Table 3, reveal that while monocyte containing cultures are activated in the presence of T3 alone, purified T cell preparations are not. For both cell preparations, similar activation was obtained with the addition of T3-5X-Amdex.

Further experiments with purified T cells verified previous findings as to the superiority of the 5X versus the 1X conjugate. The results of such an experiment are given in Table 4.

TABLE 2

|  | Control | CD3-1x-Amdex | CD3-5x-Amdex |
|---|---|---|---|
| % Blasts | 7.0 | 43.0 | 60.0 |
| % $G_0/G_1$ | 94.7 | 86.4 | 79.4 |
| % S | 1.7 | 11.1 | 17.0 |
| % $G_2/M$ | 3.6 | 2.5 | 3.5 |
| CD25 | 3.0 | 50.0 | 85.0 |
| CD71 | 2.0 | 33.0 | 73.0 |
| PCNA | 4.0 | 31.0 | 48.0 |

TABLE 3

| | % POSITIVE | | | | | |
|---|---|---|---|---|---|---|
| | T11 | Mo2 | B4 | IL2R1 | T9 | % Blasts |
| PBMC | | | | | | |
| Control | 84 | 2 | 10 | 3 | 4 | ≦2 |
| +T3 | 83 | 1 | 15 | 13 | 4 | 31 |
| +T3-5X-Amdex | 83 | 2 | 19 | 14 | 5 | 40 |
| T | | | | | | |
| Control | 95 | 3 | 0 | 3 | 4 | 6 |
| +T3 | 95 | 3 | 0 | 3 | 5 | 8 |
| +T3-5X-Amdex | 97 | 3 | 0 | 12 | 6 | 30 |

TABLE 4

| | % POSITIVE | | | | | | | |
|---|---|---|---|---|---|---|---|---|
| | T3 | T11 | Mo2 | B4 | IL2R1 | T9 | % Blasts | % S/ % $G_2M$ |
| Control | 78 | 92 | 2 | 1 | 3 | 11 | 5 | 5 |
| T3-1X-Amdex | 6 | 91 | 3 | 1 | 42 | 49 | 41 | 27 |
| T3-5X-Amdex | 1 | 91 | 3 | 1 | 59 | 69 | 65 | 41 |

The data in the following tables correspond to the indicated figures.

TABLE 5

Figure 4:
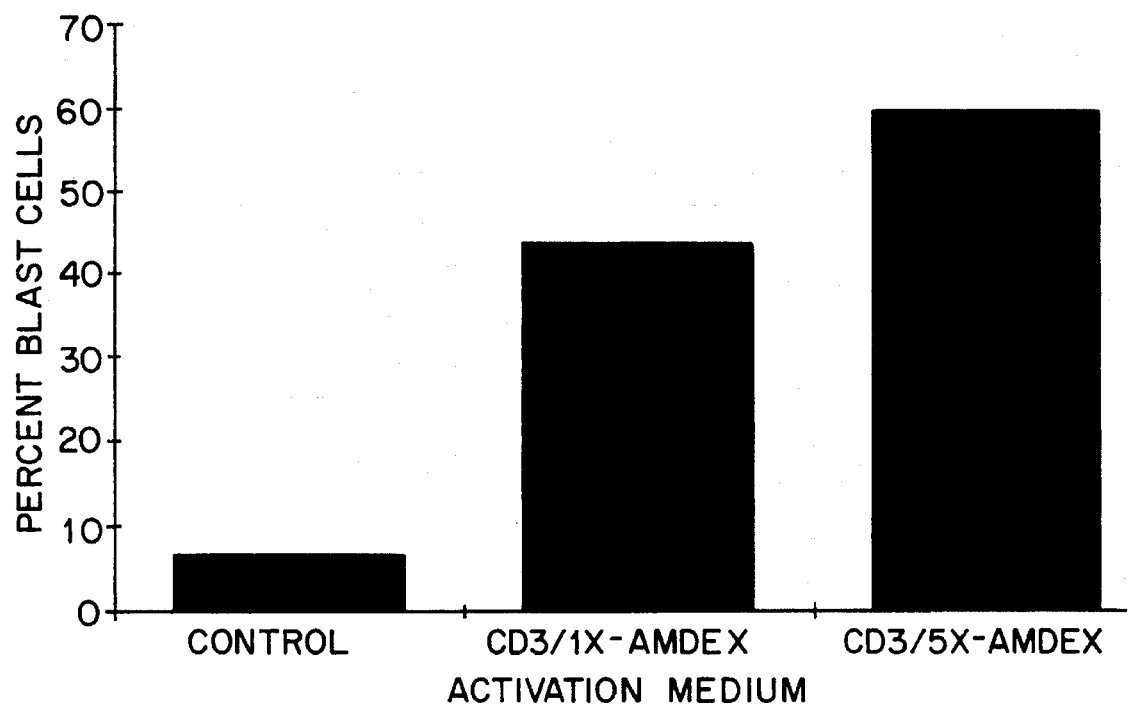
FIG. 4 graphically compares the effect of selected anti-CD3/Amdex conjugates on the formation of activated blast cells.

FIG. 4: Cell Cycle Data

| | | |
|---|---|---|
| Mean G1 = 45.7 | Mean G2 = 88.1 | % S = 1.7 |
| CV G1 = 2.1 | CV G2 = 2.1 | G2/G1 = 1.928 |
| % G1 = 94.7 | % G2 = 3.6 | Chi Sq. = 1.7 |

TABLE 6

FIG. 5: Cell Cycle Data

| | | |
|---|---|---|
| Mean G1 = 45.2 | Mean G2 = 95.5 | % S = 11.1 |
| CV G1 = 10.0 | CV G2 = 5.7 | G2/G1 = 2.115 |
| % G1 = 86.4 | % G2 = 2.5 | Chi Sq. = 1.6 |

TABLE 7

FIG. 6: Cell Cycle Data

| | | |
|---|---|---|
| Mean G1 = 46.2 | Mean G2 = 96.8 | % S = 17.0 |
| CV G1 = 11.6 | CV G2 = 6.2 | G2/G1 = 2.070 |
| % G1 = 79.4 | % G2 = 3.5 | Chi Sq. = 1.3 |

We claim:

1. An antibody-aminodextran conjugate for induction of T-cell activation and proliferation, consisting essentially of T-cell specific antibodies covalently bound to amine groups present on a water soluble aminodextran having about 7–20% by weight amine groups and a molecular weight of at least 100,000 daltons, wherein said antibodies are of a single type each specific for the same T-cell antigen and wherein the molar ratio of said antibodies to said aminodextran is greater than or equal to two.

2. The conjugate according to claim 1 wherein said aminodextran has about 15–17% by weight amine groups.

3. The conjugate according to claim 1 wherein said antibody is a monoclonal antibody.

4. The conjugate according to claim 3 wherein said antibody is an anti-CD3 monoclonal antibody.

5. An antibody-aminodextran conjugate for induction of T-cell activation and proliferation, consisting essentially of T-cell specific monoclonal antibodies and a water soluble aminodextran having a molecular weight of at least 100,000 daltons and about 7–20% by weight amine groups to which said antibodies are conjugated, wherein said antibodies are of a single type each specific for the same T-cell antigen and wherein the molar ratio of said antibodies to said aminodextran is greater than or equal to two.

6. The conjugate according to claim 5 wherein said antibody and aminodextran are covalently linked by a bridging group.

7. The conjugate according to claim 5 wherein said aminodextran contains 10–17% by weight amine groups.

8. The conjugate according to claim 7 wherein said aminodextran contains 15–17% by weight amine groups.

9. The conjugate according to claim 5 wherein said antibody is an anti-CD3 monoclonal antibody.

* * * * *